United States Patent [19]
Lenk et al.

[11] Patent Number: 5,948,441
[45] Date of Patent: Sep. 7, 1999

[54] METHOD FOR SIZE SEPARATION OF PARTICLES

[75] Inventors: Robert P. Lenk, Lambertville, N.J.; Anthony G. Durning, Yardley, Pa.; Robert J. Klimchak, Flemington, N.J.; Joel Portnoff, Richboro; Michelle L. Tomsho, Levittown, both of Pa.

[73] Assignee: The Liposome Company, Inc., Princeton, N.J.

[21] Appl. No.: 08/367,923

[22] Filed: Jan. 3, 1995

Related U.S. Application Data

[63] Continuation of application No. 08/052,815, Apr. 23, 1993, abandoned, which is a continuation of application No. 07/225,327, Jul. 28, 1988, abandoned, which is a continuation-in-part of application No. 07/164,580, Mar. 7, 1988, abandoned.

[51] Int. Cl.$^6$ .......................... A61K 9/127; A61K 9/14; B01J 13/04; B01J 13/20
[52] U.S. Cl. .......................... 424/489; 264/4.1; 264/4.3; 424/450; 424/502; 428/402.2; 436/829; 514/78
[58] Field of Search ................. 264/4.1, 4.3; 428/402.2; 424/450, 489; 436/829; 514/78; 554/83

[56] References Cited

U.S. PATENT DOCUMENTS

| | | | |
|---|---|---|---|
| 3,993,754 | 11/1976 | Rahman et al. | 424/450 X |
| 4,145,410 | 3/1979 | Sears | 424/450 |
| 4,224,179 | 9/1980 | Schneider | 264/4.6 |
| 4,235,871 | 11/1980 | Papahadjopoulos et al. | 424/450 |
| 4,420,398 | 12/1983 | Castino | 210/614 |
| 4,522,803 | 6/1985 | Lenk et al. | 424/1.1 |
| 4,529,561 | 7/1985 | Hunt et al. | 264/4.3 |
| 4,588,578 | 5/1986 | Fountain et al. | 424/1.1 |
| 4,644,056 | 2/1987 | Kothe et al. | 530/387 |
| 4,695,554 | 9/1987 | O'Connell et al. | 264/4.3 X |
| 4,737,323 | 4/1988 | Martin et al. | 264/4.3 |
| 4,752,425 | 6/1988 | Martin et al. | 264/4.6 |
| 4,766,046 | 8/1988 | Abra et al. | 264/4.3 X |
| 4,776,991 | 10/1988 | Farmer et al. | 264/4.3 |
| 4,781,871 | 11/1988 | West, III et al. | 264/4.3 |
| 4,994,213 | 2/1991 | Aitcheson et al. | 264/4.6 |
| 5,262,168 | 11/1993 | Lenk et al. | 424/450 |

FOREIGN PATENT DOCUMENTS

| | | |
|---|---|---|
| 0 214 672 | 9/1985 | European Pat. Off. . |
| 86 304 782.5 | 6/1986 | European Pat. Off. . |
| 0 208 450 | 1/1987 | European Pat. Off. . |
| 2576805 | 8/1986 | France . |
| WO85/00751 | 2/1985 | WIPO . |
| 85/00968 | 3/1985 | WIPO . |
| 85/03011 | 7/1985 | WIPO . |
| 8504578 | 10/1985 | WIPO . |
| 87/00238 | 1/1986 | WIPO . |
| WO86/00238 | 1/1986 | WIPO . |
| 86/01103 | 2/1986 | WIPO . |
| 87/00043 | 1/1987 | WIPO . |
| WO87/00043 | 1/1987 | WIPO . |
| 87/02219 | 4/1987 | WIPO . |
| 87/04169 | 7/1987 | WIPO . |

OTHER PUBLICATIONS

Klimchak, et al., "Scale–up of Liposome Products", BioPharm, Feb. 1988, vol. 1, No. 2, P 10–21.

Barneholz, et al., :A Simple Method for the Preparation of Homogenous Phospholipid Vesicles, 1977; Biochemistry, 16:2806–2810.

Bangham, et al., "Diffusion of Univalent Ions Across the Lamellae of Swollen Phospholipids", 1965; J. Mol. Biol, 12:238–252.

Gabler, Principles of Tangential Flow Filtration: Applications to Biological processing:, 1987; Filtration in the Pharmaceutical Industry, pp. 453–490.

Genovesi, "Several Uses for Tangential–Flow Filtration in the Pharmeceutical Industry", 1983; J. Pharenter. Aci. Technol. 37(3):81–86.

Huang, "Studies on Phosphatidylcholine Vesicles Formation and physical Characteristics", 1969; Biochemistry 8(1):344–351.

Olson, et al., "Preparation of liposomes of Defined Size Distribution by Extrusion Through polycarbonate membranes", 1979; Biochim. Biophys, Acta. 557:9.

Papahadjopoulos, et al., "Phospholipid Model membranes", 1967; Biochim. Biophys Act, 135:624–638.

Quirk, et al., "Investigation of the parameters affecting the separation of bacterial enzymes from cell debris by tangential flow filtration", 1984; Enzyme Bicrob. Technol., 6(5):201.

Radlett, "The Concentration of mammalian Cells in the Tangential Glow Filtration Unit", 1972; J. Appl. Chem. Biotechnol., 22:495.

Tanny, et al., "Filtration of particulates and Emulsions With a Pleated, Thin Channel, Cross–Flow Module", 1980; Separation Science and Technology, 15(3), pp. 317–337.

Tanny, et al., "A Novel membrane System for the Ultrfiltration of Oil Emulsions", 1981; ACS Symposium Series, No. 154, pp. 237–258.

Watts, et al., "Characterization of Dihyristoylphosphatidylcholine Vesicles and Their Dimensional Changes through the Phase Transition: Molecular Control of membrane Morphology", 1978; Biochemistry 17(9):1792–1801.

Zahka, et al., "Practical Aspects of Tangential Flow Filtration in Cell Separations", 1985; ACS Symposium Series, 271(0):51–70.

(List continued on next page.)

Primary Examiner—Richard D. Lovering
Attorney, Agent, or Firm—Kenneth B. Rubin; Rosanne Goodman

[57] ABSTRACT

Tangential flow filtration is used in the size separation of particles, such as liposomes and lipid particles. These particles may be passed through a tangential flow filtration device of any pore size desired. Tangential flow filter systems of various pore sizes may be used sequentially to obtain particles such as lipid particles or liposomes having a defined size range.

12 Claims, No Drawings

OTHER PUBLICATIONS

Genovesi, "Several Uses for Tangential–Flow Filtration in the Pharmaceutical Industry", 1983; J. Parenter. Aci. Technol., 37(3):81–86.

Huang, "Studies on Phosphatidylcholine Vesicles Formation and Physical Characteristics", 1969; Biochemistry 8(1):344–351.

Olson, et al., "Preparation of Liposomes of Defined Size Distribution by Extrusion Through Polycarbonate Membranes", 1979; Biochim. Biophys. Acta, 557:9.

Papahadjopoulos, et al., "Phospholipid Model Membranes", 1967; Biochim. Biophys. Acta, 135:624–638.

Quirk, et al., Investigation of the parameters affecting the separation of bacterial enzymes from cell debris by tangential flow filtration, 1984; Enzyme Microb. Technol., 6(5):201.

Radlett, "The Concentration of Mammalian Cells in a Tangential Flow Filtration Unit", 1972; J. Appl. Chem. Biotechnol., 22:495.

Tanny, et al., "Filtration of Particulates and Emulsions With a Pleated, Thin Channel, Cross–Flow Module", 1980; Separation Science and Technology, 15(3), pp. 317–337.

Tanny, et al., "A Novel Membrane System for the Ultrafiltration of Oil Emulsions", 1981; ACS Symposium Series, No. 154 pp. 237–258.

Watts, et al., "Charactrization of Dimyristoylphosphatidylcholine Vesicles and Their Dimensional Changes through the Phase Transition: Molecular Control of Membrane Morphology", 1978; Biochemistry 17(9):1792–1801.

Zahka, et al., "Practical Aspects of Tangential Flow Filtration in Cell Separations", 1985; ACS Symposium Series, 271(0):51–70).

Barenholz, et al. "A Simple Method for the Preparation of Homogenous Phospholipid Vesicles", 1977; Biochemistry, 16:2806–2810.

Bangham, et al. "Diffusion of Univalent Ions Across the Lamellae of Swollen Phospholipids", 1965; J. Mol. Biol. 12:238–252.

Gabler, "Principles of Tangential Flow Filtration: Applications to Biological Processing", 1987; Filtration in the Pharmaceutical Industry pp. 453–490.

U.S. Ser. No. 660,573, Lenk et al., filed Oct. 12, 1984 Pending .

U.S. Ser. No. 236,700, Janoff et al., filed Aug. 25, 1988 Pending.

U.S. Ser. No. 164,580, Janoff et al., filed Mar. 7, 1988 Pending.

U.S. Ser. No. 069,908, Janoff et al., filed Jul. 6, 1987 Abandoned.

U.S. Ser. No. 022,157, Janoff et al., filed Mar. 5, 1987 Abandoned.

U.S. Ser. No. 164,557, Mayer et al., filed Mar. 7, 1988 Pending.

U.S. Ser. No. 022,154, Mayer et al., filed Mar. 5, 1987 Abandoned.

U.S. Ser. No. 310,495, Cullis et al., filed Feb. 13, 1989 Pending

U.S. Ser. No. 788,017, Cullis et al., filed Oct. 16, 1985 Abandoned.

U.S. Ser. No. 622,690, Cullis et al., filed Jun. 20, 1984 Abandoned.

U.S. Ser. No. 004,762, Cullis et al., filed Jan. 7, 1987 Pending.

U.S. Ser. No. 622,502, Cullis et al., filed Jun. 20, 1984, Abandoned.

U.S. Ser. No. 946,391, Bally et al., filed Dec. 23, 1986 Pending.

U.S. Ser. No. 946,398, Lenk et al., filed Dec. 23, 1986 Pending.

U.S. Ser. No. 086,467, Popescu et al., filed Aug. 18, 1987 Pending.

ND FOR SIZE SEPARATION OF
PARTICLES

CORRESPONDING U.S. APPLICATION DATA

This application is a continuation of U.S. Ser. No. 08/052,815, filed Apr. 23, 1993, now abandoned, which is a continuation of U.S. Ser. No. 07/225,327, filed Jul. 28, 1988, now abandoned, which-in-turn is a continuation-in-part of U.S. Ser. No. 07/164,580, filed Mar. 7, 1988 and now abandoned.

BACKGROUND OF THE INVENTION

The present invention is directed to the separation of particles, such as liposomes and lipid particles, according to size using tangential flow filtration. The filtration method as disclosed permits the large scale separation of these particles into select size ranges, the size determined by the pore size of the filter employed. Any of the known tangential flow filtration devices and materials, such as the hollow fiber or tube, or the flat or pleated sheets or films, may be used. Other devices employing tangential flow filtration may also be used.

In the present invention, the terms "tangential flow filtration" and "cross flow filtration" are used interchangably, and are defined as the separation of suspended solids from aqueous or organic fluids or fluid mixture by passing or circulating a sample feed parallel or tangential to the membrane surface, with an effluent of concentrated solids continuing to flow tangential to the membrane. The pore size of the filter determines which particles will be removed in the filtrate, and those retained in the feed (retentate). For example, a sample feed stock passed through a tangential flow filtration device having a 5.0 um pore size filter allows passage of particles less than 5.0 um to pass into the filtrate. Particles larger than 5.0 um remain in the retentate.

Unlike traditional filtration processes, including those employing extrusion and ceramic filtration devices (see Martin et al., U.S. Pat. No. 4,752,425, issued Jun. 21, 1988, and Martin et al., U.S. Pat. No. 4,737,323, issued Apr. 12, 1988), the instant procedure prevents a filter cake build-up on the filter surface. Also, there is no "dead-end" extrusion of larger particles due to pressure, as the liquid is caused to flow across a membrane surface. The flow rate of the liquid is therefore maintained as it is passed over the membrane.

The present invention is directed towards the separation of particles according to size using the tangential flow filtration technique, and is specifically directed towards the size separation of particles such as liposomes and lipid particles. Liposomes and lipid particles made by any method in the art may be separated according to this technique.

Liposomes are completely closed lipid bilayer membranes containing an entrapped aqueous volume. Liposomes may be unilamellar vesicles (possessing a single membrane bilayer) or multilamellar vesicles (onion-like structures characterized by multiple membrane bilayers, each separated from the next by an aqueous layer). The bilayer is composed of two lipid monolayers having a hydrophobic "tail" region and a hydrophilic "head" region. The structure of the membrane bilayer is such that the hydrophobic (nonpolar) "tails" of the lipid monolayers orient towards the center of the bilayer while the hydrophilic "heads" orient towards the aqueous phase.

The original liposome preparation of Bangham et al. (J. Mol. Biol., 1965, 12:238–252 involves suspending phospholipids in an organic solvent which is then evaporated to dryness leaving a phospholipid film on the reaction vessel. Next, an appropriate amount of aqueous phase is added, the mixture is allowed to "swell," and the resulting liposomes which consist of multilamellar vesicles (MLVs) are dispersed by mechanical means. This technique provides the basis for the development of the small sonicated unilamellar vesicles (SUVs) described by Papahadjopoulos et al. (Biochim. Biophys. Acta., 1968, 135:624–638), and large unilamellar vesicles.

Unilamellar vesicles may be produced using an extrusion apparatus by a method described in Cullis et al., PCT Publication No. 87/00238, Jan. 16, 1986, entitled "Extrusion Technique for Producing Unilamellar Vesicles" incorporated herein by reference. Vesicles made by this technique, called LUVETS, are extruded under pressure through a membrane filter. Vesicles may also be made by an extrusion technique through a 200 nm filter; such vesicles are known as $VET_{200}s$.

Another class of liposomes that may be used are those characterized as having substantially equal lamellar solute distribution. This class of liposomes is denominated as stable plurilamellar vesicles (SPLV) as defined in U.S. Pat. No. 4,522,803 to Lenk, et al., monophasic vesicles as described in U.S. Pat. No. 4,558,579 to Fountain, et al., and frozen and thawed multilamellar vesicles (FATMLV) wherein the vesicles are exposed to at least one freeze and thaw cycle; this procedure is described in Bally et al., PCT Publication No. 87/00043, Jan. 15, 1987, entitled "Multilamellar Liposomes Having Improved Trapping Efficiencies".

Other techniques that are used to prepare vesicles include those that form reverse-phase evaporation vesicles (REVs), Papahadjopoulos et al., U.S. Pat. No. 4,235,871, issued Nov. 25, 1980.

A variety of sterols and their water soluble derivatives have been used to form liposomes; see specifically Janoff et al., PCT Publication No. 85/04578, Oct. 24, 1985, entitled "Steroidal Liposomes." Mayhew et al., PCT Publication No. 85/00968, Mar. 14, 1985, described a method for reducing the toxicity of drugs by encapsulating them in liposomes comprising alpha-tocopherol and certain derivatives thereof. Also, a variety of tocopherols and their water soluble derivatives have been used to form liposomes, see Janoff et al., PCT Publication No. 87/02219, Apr. 23, 1987, entitled "Alpha Tocopherol-Based Vesicles."

In a liposome-drug delivery system, a bioactive agent such as a drug is entrapped in or associated with the liposome and then administered to the patient to be treated. For example, see Rahman et al., U.S. Pat. No. 3,993,754; Sears, U.S. Pat. No. 4,145,410; Papahadjopoulos et al., U.S. Pat. No. 4,235,871; Schnieder, U.S. Pat. No. 4,114,179; Lenk et al., U.S. Pat. No. 4,522,803; and Fountain et al., U.S. Pat. No. 4,588,578.

In the present invention, lipid particles such as those disclosed in commonly owned copending applications, Janoff et al. U.S. patent applications Ser. No. 07/022,157, filed Mar. 5, 1987 and now abandoned, U.S. patent applications Ser. No. 07/069,908, filed U.S. Pat. No. 5,616,334, the relevant portions of which are incorporated herein similar to those for making liposomes, and have lower toxicities than the drugs when administered in their free forms. Such complexes comprise drug in a relatively high mole ratio with one or more lipids. Additionally, liposomes formed using a transmembrane pH gradient according to the methods of copending U.S. patent application Ser. No. 06/749,161, filed Jun. 26, 1985, Bally et al., entitled "Encapsulation of according to the methods of U.S. Pat. Nos. 5,077,056 and 5,616,341, both of which herein are to the invention of Bally et al.

mentioned above, liposomes are loaded with ionizable bioactive agents wherein a transmembrane pH gradient is formed across the bilayers of the liposomes, and the agent is loaded by means of this gradient. The ion gradient is generated by creating a concentration gradient for one or more charged species (for example, $H^+$ ions) across the liposome membranes. Such gradients then drive the accumulation of ionizable bioactive agents, for example, prostaglandins, or antineoplastic agents such as doxorubicin, vincristine, epirubicin, or daunorubicin into the liposomes.

More specifically, to create the concentration gradient, liposomes are prepared in the presence of a first aqueous medium, such medium being both entrapped by and surrounding the liposomes. The external medium of these liposomes is then adjusted to a more acidic or basic pH, such as by exchanging the surrounding medium. Such a process creates the transmembrane concentration gradient. If the second external medium contains an ionizable bioactive agent such as an ionizable antineoplastic agent, the $H^+$ gradient will partition the drug into the liposomes such that the free vesicle-associated bioactive agent ratios reflect $[H^+]$ in/$[H^+]$ out ratios. As disclosed in Mayer et al., identified above, antineoplastic agents such as doxorubicin, daunorubicin, epirubicin, and vincristine may be accumulated in liposomes at high drug:lipid ratios by this method, also referred to as a "remote loading" method. Such liposomes may be passed across the tangential flow filtration device and separated according to their size.

As disclosed hereinabove, when used in the process of separating liposomes or lipid particles, tangential flow filtration may be used with liposomes or lipid particles made by any of the methods known. In addition to the above-named methods, both the liposomes or lipid particles may be formed by additional or alternative processes such as shearing or sonication. In one aspect of the invention, they are formed by a homogenization technique, such as those employing homogenization, colloid milling, or size reduction process devices. When any of these devices are employed, the homogenization device may be connected directly to (in series with) the tangential flow filtration device. Alternatively, the homogenization process may be carried out independently of the filtration device.

The use of tangential flow or cross flow filtration for the gross separation of materials is known. Marinaccio et al., (WO 85/03011, published Jul. 18, 1985) disclose the process for use in the separation of biological liquids such as blood components for plasmapheresis. In this process, blood is passed tangentially to (i.e., across) an organic polymeric microporous filter membrane, and particulate matter is removed. In another use, tangential flow filtration has been disclosed for the filtration of beer (Shackleton, EP 0,208,450, published Jan. 14, 1987) specifically for the removal of particulates such as yeast cells and other suspended solids. Kothe et al., (U.S. Pat. No. 4,644,056, issued Feb. 17, 1987) disclose the use of this process in the purification of immunoglobulins from milk or colostrum, and Castino (U.S. Pat. No. 4,420,398, issued Dec. 13, 1983) describes its use in the separation of antiviral substances such as interferons from broths containing these substances as well as viral particles and cells.

Tangential flow filtration units have been employed in the concentration of cells suspended in culture media. The size of the membrane used has been chosen with regard to efficiency and speed of processing and separating the cells. Radlett (1972, J. Appl. Chem. Biotechnol., 22:495) proposes tangential flow filtration as an alternative to the more commonly used cell separation methods such as centrifugation and conventional filtration.

Similarly, the technique has been used in the separation of bacterial enzymes from cell debris (Quirk et al., 1984, Enzyme Microb. Technol., 6(5):201). Using this technique, Quirk et al. were able to isolate enzyme in higher yields and in less time than using the conventional technique of centrifugation. The use of tangential flow filtration for several applications in the pharmaceutical field has been reviewed by Genovesi (1983, J. Parenter. Aci. Technol., 37(3):81), including the filtration of sterile water for injection, clarification of a solvent system, and filtration of enzymes from broths and bacterial cultures.

The control of particle size in a population is difficult and generally has not been successful. The present invention of the use of tangential flow filtration in the separation of liposomes or lipid particles according to size is a commercially important process. The use of filters of selected sizes, and further, the sequential use or serial attachment of filters of different sizes (i.e., a filtering system) is disclosed for the separation of particles to obtain particles of a specifically desired size range.

There are problems associated with previous attempts to select liposomes according to size. For example, Huang (1969, Biochemistry, 8:344) describe a multi-step technique for the production of small unilamellar vesicles (SUVs) involving sonication, centrifugation, filtration of the population through a 0.1 um dead-end filter, and finally subjecting the filtrate to molecular sieve chromatography on a Sepharose 4B column to remove the large liposomes. Barenholz et al., (1977, Biochemistry, 16:2806) developed a technique employing sonication, centrifugation to remove large liposomes, followed by high speed centrifugation for 1 to 4 hours. This process similarly produced SUVs. Watts et al. (1978, Biochemistry, 17:1792) prepared a homogenous SUV population of dimyristoylphosphatidylcholine (DMPC) by sonication followed by centrifugation at 105,000×g.

In addition to the efforts directed at obtaining homogenous populations of SUVs, numerous attempts have been made to obtain homogenous populations of larger liposomes, i.e., MLVs. The majority of these efforts have involved the use of a series of membrane filters in an extrusion process. Such extrusion techniques involve the sequential extrusion of MLVs through filters having various pore sizes (Olson, et al., 1979, Biochim. Biophys. Acta., 557:9, and Schullery et al., 1973, Chem. Phys. Lipids, 12:75). Such a process forms a mixed population of MLVs and SUVs. These liposomes were found not to possess a homogenous, unimodal distribution with regard to size, but were in fact contaminated by liposomes of much larger and smaller size. A unimodal distribution is one in which the chi square value of the Gaussian distribution of the particle size is less than or equal to 2.0. In addition, these techniques are liposome formation techniques, as opposed to the present invention of selection of liposomes of defined size ranges from a heterogenously-sized population.

Martin et al. (U.S. Pat. No. 4,752,425, issued Jun. 21, 1988) have disclosed methods for forming liposomes of high encapsulation efficiency employing the infusion of lipids containing solvent and drug, into an aqueous solution. The method further involves the extrusion of the resulting liposomes through ceramic filters. During the infusing step, the suspensions can be diafiltered to form a filtrate of liposomes of 0.1 um and less.

There remains a difficulty in the art of obtaining a homogenous population of liposomes having a defined upper and lower size range. The present invention solves this problem by allowing selection of liposomes of a homogeneous, defined size distribution from a heterogenously-sized population. The use of filters of selected sizes is disclosed for the separation of particles of defined size. A homogeneous distribution of particles is a population of particles having a known, well-defined size distribution with essentially no particles above a certain size and essentially no particles below a certain size. As used in the present invention, the term "essentially" shall be understood to mean no more than about 10% of the particles, and preferably no more than 5% of the particles are of sizes above or below the defined size as determined by the tangential flow filter sizes. In the art, such a distribution, for example, a difference between essentially the largest and essentially the smallest particle sizes of 3, 4, 5, 10, or 100 microns, are generally not known, yet are routinely achievable in the present invention. In certain cases the resulting homogeneous distribution of liposomes or lipid particles is unimodal.

The degree to which particle size homogeneity can be obtained is influenced by the physical and chemical characteristics of the sample and the filtration conditions. For example, the viscosity and composition (charge) of the sample or the suspending solution, and the pore size and composition of the filters (thickness; presence of an asymmetric skin on the filter; charge, which influences the binding or repelling of the sample to the filter; etc.) also determine the efficiency of the filtration process and the homogeniety of the final product.

In the liposome or lipid particle sizing application, such filters may be attached downstream (in series) from a homogenization or milling apparatus; such apparatus outputs sample into the filter or filtering system (two filters, enabling the defining of particles with an upper and lower size cut-off). Alternatively, the homogenization device may be used independently, and the resulting homogenized material applied to the filtration device manually or in a separate step. In either case, the resulting filtrate (or retentate, depending on the desired product) is collected as final product. The material not passing through the filter(s) (the retentate) due to its large size may then be discarded, or alternatively recycled back through the homogenization or milling apparatus for re-sizing, and then back through the filtering device. The total yield of filtrate generally increases following each complete cycle.

Alternatively, two or more tangential flow filtration devices may be connected in parallel with the homogenization or milling apparatus. In such case the filtration devices may contain filters of different sizes, allowing separation of the same feed sample into products of differing size. In this case, if the sample is liposomes, lipid particles, or another material for sizing, the retentate may be cycled back to the homogenization or milling apparatus, to undergo further sizing adjustment.

When particles of a discrete size having both upper and lower size limits are desired, the homogenization or milling apparatus may be connected to at least two filtration devices, positioned in series, one having a filter pore size of the upper particle size limit desired, and the second having a filter pore size of the lower particle size limit. As the sample passes through the first filter, particles that are below the limit of the pore size pass through into the filtrate. The retentate may then be recycled back through the homogenization or milling apparatus for further size adjustment. The filtrate is then cycled through the next filter having the lower limit pore size. The particles smaller than this size are passed into the filtrate, and the filtrate may be discarded. The retentate thus contains all particles between the upper and lower defined size limits.

Although this technique is useful in the separation of small batches of sample feed, it is particularly useful in the large scale size separation of liposomes or lipid particles, as such separation may be easily accomplished with large volumes of material without the problems normally associated with the filtration of lipids. Such problems arise when liposomes or lipid particles are subjected to traditional "dead-end" filtration processes, as some liposomes or particles may be deformed by the pressures needed to pass them across the filter. When these particles are deformed, they may pass through pore sizes smaller than the actual particle size, and reform on the downstream side of the filter. Thus, the filtrate may be contaminated with particles of sizes outside the desired range. A second problem in the use of traditional filtration for separation of products is the product build-up on the filter surface and the eventual clogging of the membrane pores. The sweep of material tangential to the filter surface, the present technique, prevents this build-up. Additionally, in the lipid applications suggested in the present disclosure, the lower pressures employed by the tangential flow process (typically, lower than 50 psi) are less likely to cause physical damage (i.e. shearing) to the liposomes or lipid particles. Other advantages of the invention over dead-end filtration are the continuous cycling of sample, and the ability to wash out impurities from the retentate. The sample may also be concentrated by removing suspending solution from the sample, thereby resulting in a product of desired potency.

In another aspect of the present invention, the tangential flow filtration device may be used to form liposomes or lipid particles. In such a process, amphipathic materials such as lipids, and bioactive agents suspended in aqueous solutions are caused to contact one another across the membrane surfaces of a tangential flow filter. Controlled pressure delivered by a pump, and shear forces encountered at the membrane surface cause the interaction of the lipid and aqueous components and can be regulated to effect influx of one phase into the other. The control of this biphasic mixing allows the manufacture of liposomes in the defined size range desired, determined by the filter pore size and the pump pressure. More specifically, a solution containing a lipid suspension is caused to contact a first side of a tangential flow filter, while an aqueous solution, which can contain a bioactive agent such as a drug, is infused or injected into the area surrounding a second side of the filter. Pressures delivered to the aqueous side of the filter via a pump cause the passage of the aqueous solution across the filter, through the pores, to the lipid-containing side. Liposomes form at the lipid side of the filter.

In particular, a lipid suspended in an organic solvent, for example, egg phosphatidylcholine in ethanol at about 100–1000 mg/ml is passed in the extracapillary space of a hollow fiber tangential flow filter, for example; and an aqueous solution, such as for example, buffer or a saccharide solution is passed through the lumen of the filter. In response to applied pump pressures, the aqueous solution passes through the pores of the tangential flow filter and forms liposomes in the lipid solution on the extracapillary side. Such a system is a continuous flow system, which allows formation of large volumes of liposomes. In an alternative method, dynamic rotary flow filtration can be employed in a similar technique to form liposomes. Such a filtration process employs a rotary flow filtration unit such as the Benchmark Rotary Filtration unit (Membrex, Inc., Garfield, N.J.). In this method, the lipid suspension is passed through the lumen of the filter, and the aqueous solution passed through the extracapillary space. The flat, cylindrical filter, attached to a rotating shaft, produces vortices, when rotated, that cause the aqueous solution to pass through the filter into the lumen. At the interface between the filter surface and the lumen, the aqueous solution forms liposomes with the lipid circulating in the lumen. This liposome product is then removed from the lumen.

Another aspect of the present invention which also employs tangential flow filtration is the separation of liposomes or lipid particles from solvents or, alternatively, from free (unentrapped or unassociated) drug in the preparation. Such extraliposomal or extralipid particle materials may be removed by their ability, for example, to pass through the membrane pores, while the liposomes or particles remain circulating in the retentate. The use of filter sizes smaller than the desired liposome or particle size permits the passage of these smaller solvent or free drug molecules through the filter pores, while retaining the desired product. Such a use minimizes, or may eliminate the need for exhaustive rotary evaporation or related techniques for solvent removal. It also eliminates the need for chromatographic separation of free particulates such as free drug, from the final preparation. Both of these processes may be simultaneously performed with the size separation function of the instant invention. Alternatively, a liposome or particle population may be exposed to a solvent- or free drug-removal step prior to the size separation (filtration) step. All processes, however, may be performed by the same device, by choosing the appropriate filter size specific to the function desired. The filter size chosen depends on the size of the molecules or particles to be removed.

Still another use for the tangential flow filtration device is in the separation and classification of microcapsules, suspensions, emulsions, and other small particle systems, such as mixture of different cells, according to size.

An additional advantage of the present invention is that the separations can be done aseptically. Aseptically preparing liposome or lipid particles of defined size distribution has been an ongoing problem.

SUMMARY OF THE INVENTION

This invention is directed to a process for separating particles according to size, from a mixture of particles suspended in a liquid, which involves subjecting the mixture to tangential flow filtration with a first filter of a first pore size and then subjecting the filtrate to tangential flow filtration with a second filter of second, smaller pore size. The process may be performed with particles comprising liposomes or lipid particles. These liposomes or lipid particles may additionally comprise a bioactive agent, such as a polyene antifungal agent such as amphotericin B. In such a case, the mole ratio of amphotericin B to the lipid of the liposomes or lipid particles is about 1 mole % to about 60 mole %, more preferably about 16 to about 50 mole %., and most preferably about 33 mole %.

The tangential flow filtration step employs a first filter of first pore size between about 10 and about 0.2 um, preferably about 5 um, which excludes particles above the defined cutoff, and a second filter of second pore size of between about 2000 molecular weight and about 2 microns, preferably about 1.0 um.

In the case where the particles are lipid particles, they preferably comprise dimyristoylphosphatidylcholine and dimyristoylphosphatidylglycerol in about a 7:3 mole ratio and about 33 mole % amphotericin B.

Alternatively, the bioactive agent can comprise an aminoglycoside such as gentamicin, and the particles can be liposomes, such as an SPLV. These SPLVs may comprise phosphatidylcholine. These liposomes may be size selected by filtration through a first pore size of about 5 um and a second pore size of about 1 um. The particles may also be milled by homogenization such as colloid mill to reduce their size. The resulting particles may have a homogenous size distribution, and may be multilamellar or unilamellar.

In another embodiment of the present invention, the tangential flow filtration process can be employed to remove extraliposomal or extralipid particle material from a mixture comprising liposomes or lipid particles suspended in a liquid. In such a case, the the extraliposomal or extralipid particle material may be in an organic solvent, such as DMSO. Alternatively, the process can be used to remove unentrapped or unassociated bioactive agent.

In yet another embodiment of the present invention, the tangential flow filtration method can be employed to prepare a liposome or lipid particle wherein a solution containing lipid is caused to contact a first side of a filter in tangential flow filtration apparatus while an aqueous solution is infused or injected at a second side of the filter of the tangential flow filtration apparatus. This process may be performed using a dynamic rotary filtration or a hollow fiber filtration.

DESCRIPTION OF THE INVENTION

The separation of particles, specifically liposomes and lipid particles, using the tangential flow filtration technique is described. More specifically, this separation results in the size separation of the liposomes and lipid particles. These liposomes or lipid particles may entrap or be associated with a bioactive agent, i.e. an agent having biological activity, such as for example, a drug, hormone, protein, dye, vitamin, or imaging agent.

For example, obtaining lipid particles such as high drug:lipid complexes (HDLCs), described in U.S. Pat. No. 5,616,341, and incorporated herein by reference, which comprise amphotericin B, such particles being in about the 1 micron to about 5 micron (um) size range, the initial heterogenously-sized sample having a particle size range of about 0.1 to about 50 um feed is tangentially filtered using a about 5.0um pore size filter. The filtrate contains particles smaller than about 5.0 um, and the retentate contains particles larger than about 5.0 um. The filtrate is then filtered using a smaller pore size, such as about 1.2 um pore size. The pore size of this second filter is in no way limited but may be as small as available, for example, about 2000 molecular weight. In the present invention, filters of about 1.2 um and about 0.2 um are preferred. When the about 1.2 um filter is used following the about 5.0 um filter, the filtrate contains all particles smaller than about 1.2 um such as fines, and the retentate is the final product having the required size range of about 1.2 to about 5.0 um. If a greater size is needed or acceptable, then, for example, a about 10 um filter can be employed to obtain the upper size cutoff.

The filters employed in the tangential flow filtration device of the present invention may be chosen from a wide range of organic polymeric filters. Such filters include but are not limited to microporous membranes of nylon, polyvinylidene fluoride (PVDF), cellulose acetate/nitrate, polysulfone, polypropylene, and polyamide. Other filters such as ceramic filters and metallic filters may also be used.

Membranes having a charged surface, such as those containing carboxyl or sulfonic anionic functional substituents or nylon charged membranes may also be used. Such charged membranes may be used efficiently when the preparation contains charged lipids. Membranes having an asymmetric structure, such as those used in the processes of reverse osmosis, dialysis, and ultrafiltration may also be used. The preferred membranes, of compositions described above, are of the microporous type, having symmetrical structure across the membrane. Suitable filter assemblies for containing the membranes include but are not limited to the cartridges containing either hollow tubes or fibers, or rolled flat or pleated sheets mounted on plate frames. A stirred cell apparatus may also be employed as a tangential flow filtration device (available from Amicon Corp., Danvers, Mass.). In such a system, a stirring paddle circulates sample feed in a motion tangential to the surface of the membrane.

The membranes most suited for the applications as herein described are those that are resistant to solvents, and those that are amenable to sanitization, or sterilization; in the latter case by such techniques as autoclaving, steam flushing, irradiation, or ethylene oxide exposure. They should be sufficiently hydrophilic or hydrophobic to allow removal of aqueous or organic solvents from the sample. The filters named above would be chosen according to the specific functions they are to perform (solvent removal, free drug removal, and/or size separation, to name a few). For example, the polypropylene and ceramic membranes withstand organic solvents, while the polysulfones and cellulose acetate/nitrate membranes generally do not. Any of the above-mentioned membranes may be used for aqueous solvent removal, or for size separation of the liposomes or lipid particles. Use of such membranes is limited only by the diameter of the products desired, and the availability of the appropriate pore size.

When the polypropylene and nylon (hydrophobic) membranes are employed, best results are obtained when the membranes are wetted with a water-miscible organic solvent such as ethanol, prior to use. This wetting step may be performed for several minutes by recirculating the solvent through the membrane. The solvent is then removed by the flushing of the membranes with aqueous solution such as deionized water or 0.9% saline.

The filtration may proceed at any temperature, to be determined by the temperature restrictions of the lipids or drug used. For example, the process may be performed in the cold at about 4° C. to about 25° C. The sample is circulated through the filtration apparatus by the force provided by a pump. Pumps which may be employed include the following types: positive displacement rotary lobe, gear, centrifugal, diaphram, or peristaltic. In the present invention, a rotary lobe pump is preferred. The operating pressure (inlet pressure, which affects the filtration rate) is dependent on a number of variables, such as the volume, viscosity, and composition of the sample, as well as the composition, and surface area of the membrane employed. The operating pressure is generally low on each side of the filter as is the pressure differential across the filter. In general, in order to increase the separation rate, the flow rate is increased. As the viscosity of the sample increases, or the size of the sample particles approach the size of the filter pore rating, the pressure applied can be less; pressure parameters are also dependent upon the filter material employed and the sample composition. Finally, if the filter is charged, the charge of the sample passing through (like charge, or opposite charge) may determine the rate at which it flows through the filter (more slowly, or more quickly, respectively), and therefore determines the pump pressure applied. The filter configuration (hollow fiber or tube, or flat sheet) is an additional variable to the pressure setting. Similarly, further considerations, such as the adsorption and/or occlusion of the micropores of the membrane with any of the substituents of the sample may dictate the most efficient rate of filtration. For example, such occlusion may necessitate replacement of the filter following processing of a certain sample volume. Determination of pressure parameters is within the skill of those working in the art of low pressure filtration.

In general, when used in the present invention, the maximum psi of hollow fiber film filters (polypropylene, polysulfone, and the like) is about 50 psi, and the ceramic hollow fiber filters is about 150 psi, while the flat sheet membranes can withstand similar pressures. Choice of the appropriate pressures are best determined by those skilled in the art of lipid products and tangential flow filtration. Pressures that are too high might cause extrusion of the liposomes or particles, cake formation, or liposome breakage by shear forces.

The sample is preferably recirculated multiple times, the number of circulations determined by the volume, viscosity and charge of the sample. For example, as the volume and/or viscosity of the sample is increased, the time of recirculation increases. The lipid concentration is also determinative of the time of recirculation through the filter, and the rate of the filtration. In a highly viscous preparation, for example, the smaller particles may not reach the filter surface to be eliminated into the filtrate. Such a case may require dilution of the feed stock and/or reduction of the recirculation rate. In addition, the time of recirculation of the sample may be increased.

The duration of processing would be chosen when the yield of particles of required size is optimized, and when the sample is not alternatively overprocessed, thus containing many fines. The operator may remove an aliquot of the sample while it is in process and examine its size for example, under a light microscope with an ocular micrometer, or by using quasi-elastic light scattering (QELS) or Malvern particle sizer techniques, to determine the general size of the population, and then either continue or stop the filtration.

As the effluent (filtrate) is collected from the filter, aqueous or organic solution (such as for example sterile buffer or 0.9% saline) may be added to the retentate at the same rate at which filtrate is removed in order to maintain the volume. This diafiltration process enhances the particle yield obtained. In principle, for removal of about 90% of a species (such as for example, particles, such as liposomes or lipid particles) that may freely pass through the filter (i.e., a zero rejection coefficient), one can maintain the volume of the retentate while washing with buffer about 2.3 times the volume of the retentate. To remove about 99% of the desired species, the volume of wash through the filter is 2×2.3 times the retentate volume. Specifically, 1.0 ml of wash replaces 1.0 ml filtrate removed from the system. Diluted filtrate obtained by this diafiltration process may be concentrated later, using tangential flow filtration. Alternatively, a series of dilutions and concentrations may be used to increase the passage of the species of interest into the filtrate. Alternatively, the entire sample can be recirculated through the filter which would not require addition of aqueous solution.

As described hereinabove, two or more tangential flow filtration devices may be connected in series, such as with a pump between the filtration units to provide ample flow for the second filtration, resulting in a product of specific size separation having upper and lower size limits. Alternatively or additionally, a homogenization apparatus can be connected to the filtration device, and the homogenized sample passed directly from this apparatus into the filtration system.

A pump can be attached between the homogenizer and the filter to maintain the flow rate of the feed into the filter. The filtrate product can pass from the filter to a holding tank while the retentate not sufficiently homogenized can be pumped back to the homogenizer to undergo further size adjustment prior to further processing in the filter.

The liposomes or lipid complexes of the present invention can entrap or complex with, respectively, any bioactive agent such as drugs. In the case of liposomes, drugs may be entrapped or associated with the liposomes, such as for example, the aminoglycosides such as neomycin B, paromomycin, ribostamycin, lividomycin, kanamycin A, kanamycin B, amikacin, tobramycin, gentamicin, netilmicin, streptomycin, dihydrostreptomycin, and sisomicin. Other drugs that may be entrapped or associated with the liposomes of the invention are for example, arachidonic acid metabolites and their structural analogs and synthetic enzyme inhibitors, and subclasses thereof, such as for example, the prostaglandins A through F, $G_2$, $H_2$ and thromboxanes $A_2$ and $B_2$, the prostacyclines, and leukotrienes, and in particular prostaglandin $E_1$ ($PGE_1$). Still other bioactive agents that can be entrapped or associated with the liposomes of the invention are the antineoplastic agents. The antineoplastic agent can be, for example, an anthracycline such as doxorubicin, daunorubicin, or epirubicin, a vinca alkaloid such as vinblastine or vincristine, a purine or pyrimidine derivative such as 5-fluorouracil, an alkylating agent such as mitoxanthrone, mechlorethamine hydrochloride or cyclophosphamide, or an antineoplastic antibiotic such as mitomicin or bleomicin. Other bioactive agents that are complexed with the lipid to form lipid particles that can be filtered by the methods of the invention are the polyene antifungal agents such as nystatin, pimaricin, candicidin, filipin, and preferably, amphotericin B.

As discussed above, the liposomes or lipid particles of the present invention may be made by any of the techniques known in the art for their formation. In one embodiment of the present invention, a homogenization device is used to process the liposomes or particles. Such a homogenization device includes but is not limited to devices such as the Gaulin type or Microfluidizer (Microfluidics, Inc.) type homogenizer, a colloid mill or similar milling device, or a size reduction device that forms liposomes or lipid particles through an extrusion process (Cullis et al., PCT Publication No. 87/00238, Jan. 16, 1986, entitled "Extrusion Technique for Producing Unilamellar Vesicles").

In the homogenization aspect of the invention, a homogenizer or colloid mill is connected to a pump set to deliver about 1 to about 4 l/min to the mill with about 10 to about 15 psi back pressure, the sample feed is milled and the product is collected in a tank. If the desired size of the liposomes or particles is smaller than that which may be obtained by one pass through the mill, the feed may be reprocessed through the colloid mill a second (or multiple) time. As with the filtration technique, determination of having reached the end point may be made by the examination of an aliquot of milled sample under the light microscope, QELS, Malvern, or similar technique. Ideally, the end point of the milling step is reached when most of the particles or liposomes fall within the size range of the final product. The size separation of the milled product then may proceed using the tangential flow filter, to select the specific sizes desired.

In the processing of 15 liters of lipid particles containing amphotericin B as described above, about 18 cycles through the mill were required prior to the filtration step. This number would be expected to vary with the above-mentioned conditions. The lipid concentration used may further determine the number of processing cycles required. The amount and type of drug would also determine the milling time required, as a highly viscous sample would not be expected to filter efficiently.

In the case where the filtration process can be used to remove solvent, the achievement of the end point (for example, about 99% of solvent removed) is determined by the standard techniques of gas chromatography. In the case where it is desired to remove free drug from the preparation, determination of having reached the end point of less than about 99% of free drug remaining (when diafiltration, as described above, is used), is by for example, colorimetric analysis.

In another embodiment of the present invention, liposomes or lipid particles are formed using the process of tangential flow filtration. In this process, for example, a drug such as amphotericin B suspended in a solvent, for example, DMSO, is fed to the extracapillary space of a hollow fiber filter from a reservoir. Lipid in solvent such as methylene chloride is similarly fed through tubing into the lumen of the hollow fiber filter. The amphotericin B in DMSO enters through the pores of the filter into the lumen, in response to a higher pressure maintained on the filtrate side, where it complexes with the lipid, forming particles. The solvents are removed during the same process by diafiltration with a suitable replacement solvent such as saline solution, buffered aqueous solution, water or ethanol. The concentrations of lipid and bioactive agent, if included, can be those employed in preparing liposomes or lipid particles by other methods.

In another example of liposome formation using the tangential flow filtration process, liposomes of defined size are remote loaded with ionizable bioactive agents, such as prostaglandin $E_1$ ($PGE_1$). In this liposome formation method, an aqueous solution, such as for example, an aqueous maltose solution at relatively acidic or basic pH (in the case of $PGE_1$, this solution is relatively basic), is circulated in the lumen of a hollow fiber filtration device of for example, polypropylene with 0.1 um pore size, at a pressure of about 2.0 psi. The lipid, for example, egg phosphatidylcholine (EPC), is similarly fed through tubing into the extracapillary space of the filter. The maltose in solution exits through the pores into the extracapillary space, in response to a higher pressure maintained on the lumen side, where it contacts the lipid, forming liposomes. The bathing solution of the formed and size-selected liposomes is then adjusted to a relatively basic or acidic pH (for example, in the case of $PGE_1$, this adjustment is made to a relatively more acidic pH), and the ionizable bioactive agent is admixed with the liposomes.

In the size selection of liposomes that had been remote loaded with ionizable bioactive agents according to the methods disclosed above, and specifically loaded by these methods with ionizable antineoplastic agents such as doxorubicin, the procedures are as follows. The liposomes are formed using egg phosphatidylcholine and cholesterol (3:1 weight ratio) in acidic buffer, preferably about 300 mM citric acid at about pH 4.0. The resulting liposomes may be size reduced using any methods known in the art, such as homogenization, for example, by Gaulin or Microfluidizer homogenizer, or extrusion. These liposomes are filtered by tangential flow filtration methods, in buffer of pH about 4.0, first through a filter having a pore size of about for example 0.2 um, the filtrate then passing through a second tangential flow filter having a pore size of for example, about 0.1 um. The retentate is the final product, having liposomes of sizes between about 0.1–0.2 um. The liposomes are then sterile filtered through a filter of pore size about 0.20 um. Following the adjustment of the pH to about 7.5 using an appropriate buffer, such as sodium carbonate, doxorubicin is added and is accumulated into the liposomes as a result of the transmembrane pH gradient. Alternatively, the retentate can be lyophilized and stored until use. Upon use, the lyophilizate can be reconstituted using buffer of relative basic pH, such as at about pH 7.5. Additionally, the retentate (from the about 0.20 um tangential flow filtration) can be homogenized using any device known for this purpose, such as a Gaulin homogenizer. In this case, after the sample is passed through the first tangential flow filter, the retentate, above the upper size limit of the desired product, can be recirculated back into the homogenizer for further processing.

For the liposomes or lipid particles of the present invention, any suitable lipids may be employed. The term lipid as used herein shall mean any suitable material resulting in a bilayer such that a hydrophobic portion of the lipid material orients toward the bilayer while a hydrophilic portion orients toward the aqueous phase. Lipids include highly hydrophobic components such as triglycerides, sterols such as cholesterol, and amphipathic lipids. The lipids which can be used in the liposome formulations of the present invention are for example, the phospholipids, such as phosphatidylcholine (PC), phosphatidylethanolamine (PE), phosphatidylserine (PS), phosphatidylglycerol (PG), phosphatidic acid (PA), phosphatidylinositol (PI), sphingomyelin (SPM), and the like, alone or in combination. The phospholipids can be synthetic or derived from natural sources such as egg or soy. Synthetic phospholipids such as dimyristoylphosphatidylcholine (DMPC) and dimyristoylphosphatidylglycerol (DMPG) may also be used. In the preferred embodiments, the phospholipid egg phosphatidylcholine (EPC), is used. The liposomes can also contain other steroid components such as polyethylene glycol derivatives of cholesterol (PEG-cholesterols), coprostanol, cholestanol, or cholestane, and combinations of EPC and cholesterol. They may also contain organic acid derivatives of sterols such as cholesterol hemisuccinate (CHS), and the like. Organic acid derivatives of tocopherols may also be used as liposome-forming ingredients, such as alpha-tocopherol hemisuccinate (THS). Both CHS- and THS-containing liposomes and their tris salt forms may generally be prepared by any method known in the art for preparing liposomes containing these sterols. In particular, see the procedures of Janoff, et al., PCT Publication No. 85/04578, filed Oct. 24, 1985, entitled "Steroidal Liposomes," and Janoff, et al., PCT Publication No. 87/02219, Apr. 23, 1987, entitled "Alpha-Tocopherol Based Vesicles,". The liposomes may also contain glycolipids.

During preparation of the liposomes or the lipid particles, organic solvents may be used to dissolve the lipids. Suitable organic solvents are those with a variety of polarities and dielectric properties, which solubilize the lipids, and include but are not limited to chloroform, methanol, ethanol, and methylene chloride. As a result, solutions (mixtures in which the lipids and other components are uniformly distributed throughout) containing the lipids are formed. Solvents may be used to solubilize the bioactive agents (drugs), and where necessary, any of the above-named solvents, including dimethyl sulfoxide (DMSO) may be used. Solvents are generally chosen on the basis of their biocompatability, low toxicity, and solubilization abilities.

The liposomes or lipid particles of the invention may entrap or be associated with bioactive agents such as drugs. Such drugs may be used in both the size selection embodiments or the liposome-forming embodiments of the tangential flow filtration processes. Suitable bioactive agents for these uses include but are not limited to the polyene antifungal agents such as nystatin, pimaricin, candicidin, filipin, and preferably, amphotericin B. Other bioactive agents that may be used include but are not limited to antibacterial compounds such as the aminoglycosides, for example, gentamicin, as stated above, antiviral compounds such as rifampacin or azidothymidine (AZT); anti-parasitic compounds such as antimony derivatives, antineoplastic compounds such as vinblastine, vincristine, mitomycin C, doxorubicin, daunorubicin, methotrexate, and cisplatinum, among others; proteins such as albumin, toxins such as diptheria toxin, enzymes such as catalase, hormones such as estrogens, neurotransmitters such as acetylcholine, lipoproteins such as alpha-lipoprotein, glycoproteins such as hyaluronic acid, immunoglobulins such as IgG, immunomodulators such as the interferons or the interleukins, dyes such as Arsenazo III, radiolabels such as $^{14}$C, radio-opaque compounds such as $^{99}$Te, fluorescent compounds such as carboxy fluoroscein, polysaccharides such as glycogen, cell receptor binding molecules such as estrogen receptor protein, nonsteroidal anti-inflammatories such as indomethacin, salicylic acid acetate, ibuprofen, sulindac, piroxicam, and naproxen; anti-inflammatories such as dexamethasone, antiglaucomic agents such as timolol or pilocarpine, anesthetics such as dibucaine, nucleic acids such as thymine, polynucleotides such as RNA polymers, cardiovascular agents such as alpha-blocker, beta-blocker, calcium channel blockers, ACE inhibitors, and the like, CNS agents and prostaglandins.

In the liposome or lipid particle hydration step, aqueous solutions such as distilled water (e.g., USP water for injection), saline (0.9%), or aqueous buffers may be used. Aqueous buffers that may be used include but are not limited to buffered salines such as phosphate buffered saline "PBS," tris-(hydroxymethyl)-aminomethane hydrochloride "tris" buffers, or glycine buffers at pH of about 7.0 to 7.5, preferably 7.2.

The liposomes of the present invention may be dehydrated (or lyophilized) thereby enabling storage for extended periods of time until use. Standard freeze-drying equipment or equivalent apparatus may be used to lyophilize the liposomes. Liposomes may also be dehydrated simply by placing them under reduced pressure and allowing the suspending solution to evaporate. Alternatively, the liposomes and their surrounding medium may be frozen in liquid nitrogen prior to dehydration. Such dehydration may be performed in the presence of one or more protectants such as protective sugars, according to the process of Janoff et al., PCT 86/01103, published Feb. 27, 1986, and incorporated herein by reference. In this invention, dehydration may be performed either prior to or following the tangential flow filtration (size separation) step.

The preparations of the present invention can be used therapeutically in animals (including man) in the treatment of a number of infections or conditions which require: (1) repeated administrations; (2) the sustained delivery of a drug in its bioactive form; or (3) the decreased toxicity with substantially equivalent or greater efficacy of the free drug in question. Such conditions include but are not limited to fungal infections, both topical and systemic such as those that can be treated with antifungal agents such as nystatin and amphotericin B and the bacterial infections that respond to antibiotic chemotherapy.

The mode of administration of the preparation may determine the sites and cells in the organism to which the compound will be delivered. The liposomes and lipid particles of the present invention can be administered alone but will generally be administered in admixture with a pharmaceutical carrier selected with regard to the intended route of administration and standard pharmaceutical practice. For instance, delivery to a specific site may be most easily accomplished by topical application (if the infection is external, e.g., on areas such as eyes, skin, in ears, or on afflictions such as wounds or burns). Such topical applications may be in the form of creams, ointments, gels, emulsions, or pastes, for direct application to the afflicted area. Alternatively, the preparations may be injected parenterally, for example, intravenously, intramuscularly, or subcutaneously. For parenteral administration, they can be used, for example, in the form of a sterile aqueous solution which may contain other solutes, for example, enough salts or glucose to make the solution isotonic. Other uses, depending on the particular properties of the preparation, may be envisioned by those skilled in the art.

For administration to humans in the curative or prophylactic treatment of fungal or bacterial diseases, the prescribing physician will ultimately determine the appropriate dosage for a given human subject; this can be expected to vary according to the age, weight, and response of the individual as well as the nature and severity of the patient's symptoms. The dosage of the drug in the liposomal or lipid particle form will generally be about that employed for the free drug. In some cases, however, it may be necessary to administer dosages outside these limits.

The following examples are given for purposes of illustration only and not by way of limitation on the scope of the invention.

PREPARATION

Amphotericin B particles (HDLCs) were formed according to the following procedure: Amphotericin B (78.03 mg) was added to 867 ml of DMSO in a 5 liter pressure can, and stirred to dissolve for 3 hours at 25° C. This solution was sterile filtered into a second 5 liter pressure can at 25° C.

Dimyristoylphosphatidylcholine (DMPC) (60 g) and 26.4 g of dimyristoylphosphatidylglycerol (DMPG) (a 7:3 mole ratio) was combined with 21 L of methylene chloride in a 50 L pressure vessel, and mixed to dissolve completely. It was then sterile filtered through a 0.22 um TEFLON® (tetrafluoroethylene) filter into a 50 L triple-neck round bottom flask. The amphotericin B/DMSO mixture was added to the lipid solution in the round bottom flask, (for a 33 mole % amphotericin B solution) followed by the addition of 4.32 L of 0.9% sterile saline to the round bottom. The suspension was mixed with a banana paddle. The methylene chloride was removed by a vacuum distillation process (750 mm Hg) at 40° C. in process for 20 hours. After this time 5 L remained in the flask.

EXAMPLE 1

To the 5 L of lipid/amphotericin B particles of the Preparation was added 5 L of 0.9% sterile saline. Four liters of this solution (at 4.04 mg/ml amphotericin B) was connected from the reservoir containing it, through silicone peristaltic tubing, to inlet and outlet ports of a Baxter Travenol (Model 15.11) hollow fiber tangential flow filtration dialysis unit, equipped with a filter membrane of regenerated cellulose. A Watson Marlow peristaltic pump was set to deliver 250 ml/minute to the tangential flow device.

A 4 L sterile 0.9% saline bath was similarly attached and pumped to the ports of the Baxter Travenol device leading to the extracapillary space of the dialysis unit. A similar peristaltic pump was set to deliver saline to the unit at a rate which maintained a constant volume in each reservoir. The saline tubing was attached to the device so that a countercurrent flow of saline to lipid particles was achieved. The solutions circulated countercurrently for 1 hour, then the saline solution was changed to fresh saline. Five changes were made after 1 hour circulations. This process removed the DMSO from the solution.

Analysis of pre- and post-dialysis DMSO was determined by using standard gas chromatography techniques using tetrahydrofuran (THF). Pre-dialysis DMSO was determined to be 7.75%, and post-dialysis DMSO 0.05%. The resulting volume was 4.3 L.

EXAMPLE 2

Three liters of the dialyzed particles of Example 1 above were selected according to size according to the following technique: A Pellicon tangential flow filtration unit equipped with a 5 um pore size 1 ft.$^2$ Durapore flat sheet membrane (plate and frame configuration) in 2 filter packs (½ ft.$^2$ each, separated by polypropylene channels) was used to size the particles. A reservoir containing the 3 L sample was connected with silicone peristaltic tubing to a Watson Marlow (Model 603 U/R) peristaltic pump set to deliver 4 L/minute, then connected to the inlet port of the Pellicon device. The inlet pressure was set at 3 psi. The psi at the Pellicon exit port (retentate) was 1 psi and that at the filtrate port was 1.6 psi. The flow rate of the filtrate was about 32 ml/minute and was pumped from the Pellicon device using a Watson Marlow (Model 501 U/R).

After 2500 ml of filtrate was collected, the sample was diafiltered by adding 32 ml/minute of sterile 0.9% saline to the reservoir. The process continued until 1530 ml additional filtrate was collected for a total of 4030 ml of filtrate/ diafiltrate. The resulting concentration of DMSO as determined by standard gas chromatography was 0.01%. The particle size as determines by Malvern particle sizing technique was less than 1.0 um to 4.7 um.

EXAMPLE 3

Lipid particles of a size range of less than 1.0 um to 50 um were, prepared according to the Preparation, processed according to Examples 1 and then filtered by the process of Example 2 using a 5 um filter size, yielding particles of size up to 4.5 um. Three liters of these particles were placed in a reservoir and the reservoir attached by silicone peristaltic tubing (with a pump) to the inlet port of a Gelman 1.2 um (Acroflux, pleated flat sheet configuration, 900 cm$^2$) tangential flow filter apparatus, and the flow rate set at 4 L/minute. The filtrate (particle size up to 1.2 um) was collected through the filtrate port and the retentate was recirculated to the reservoir. Retentate (410 ml) was collected.

EXAMPLE 4

Liposomes were made containing gentamicin by means of the SPLV process (in accordance with the procedures of Lenk et al., U. S. Pat. No. 4,522,803, issued Jun. 11, 1985, and herein incorporated by reference), employing gentamicin (286 g) dissolved in 0.9% weight to volume of aqueous saline solution (15.1 L) and egg phosphatidylcholine (490 g) dissolved in methylene chloride (24.5 L). The SPLV liposomes were diluted with 0.9% aqueous saline solution. These liposomes of less than about 1.0 um–5 um in size were concentrated from a volume of 8.2 liters using a Microgon Krosflow II (Microgon, Inc., LaGuna Hills, Calif.) tangential flow filtration system according to the methods of Example 2. The filter pore size was 0.2 um and the surface area was 10 ft.². A reservoir containing the 8.2 L of gentamicin liposomes was connected to the inlet port of the Krosflow filter using silicone peristaltic tubing. Silicone tubing attached to the filter outlet led retentate back into the reservoir. A Watson Marlow peristaltic pump was used to pump product into the filter (flow rate about 4 L/min. inlet pressure at 3–10 psi, filtrate flow rate about 75 ml/min.).

After the concentration step was completed, the filtrate was assayed for gentamicin concentration using standard calorimetric techniques, and found to have a concentration of 7.92 mg gentamicin/ml. The diafiltration step was then performed according to Example 2. Pumping conditions were as above while approximately 9 liters of saline was added to the system for diafiltration. The filtrate was monitored for gentamicin, the final 50 ml had a concentration of 0.10 mg/ml. This indicated that the free gentamicin in the concentrate had been decreased by 99% from the point before diafiltration.

Gentamicin flows freely through the pores of the 0.2 um filter and therefore the concentration found in the filtrate is indicative of the free gentamicin in the concentrate (the retentate).

EXAMPLE 5

Amphotericin B particles (HDLCS) were formed according to the following procedure: Amphotericin B (337.5 g) was added to 3375.0 ml of DMSO, and stirred to dissolve for 5.5 hours at 25° C. This solution was sterile filtered into a 5 liter pressure can at 25° C.

Dimyristoylphosphatidylcholine (DMPC) (264.3 g) and 109.9 g of dimyristoylphosphatidylglycerol (DMPG) (a 7:3 mole ratio) were combined with 35.2 L of methylene chloride in a 40 L pressure vessel, and mixed to dissolve completely. This solution was then sterile filtered through a 0.22 um TEFLON™ filter into a 140 L processing tank. Methylene chloride (39.1 L) was sterile filtered through a 0.22 um TEFLON™ filter and added to the 140 L tank. The amphotericin B/DMSO mixture was added to the lipid solution, (for a 33 mole % amphotericin B solution) followed by the addition of 16.5 L of 0.9% sterile saline to the tank. The suspension was mixed with a marine propeller. The methylene chloride was removed by sterile $N_2$ gas purging. The final temperature was less than 40° C. after about 13 hours. Sterile saline (7.0 L) was added to the batch for a total volume in the process vessel of about 27 L.

This product was circulated through a Gifford-Wood colloid mill with for about 5 hours to decrease the average size of the lipid particles to about 5.0 um. After milling, the product was circulated through a Romicon 5.0 um ceramic tangential flow filter (2 ft²) using an Alfa Laval rotary lobe pump at an average flow rate of 24 gpm, for a total of about 10 hours. Sterile physiological saline (410 L) was added in 30 L aliquots through a top port of the 140 L vessel. The average filtration rate was about 500 ml/min. The filtrate was then passed into a reservoir, and concentrated by passage through a 1.2 um Romicon 2 ft² ceramic filter driven by an Alfa Laval rotary lobe pump at a flow rate of about 36 gpm; (about 14.5 hours) the filtration rate was about 500–600 ml/min. This filtration removed the particles 1.2 um and less in the filtrate. The 1.2 um retentate was collected as the final product.

EXAMPLE 6

Liposomes containing gentamicin were made by the SPLV process according to the methods of Example 4. These liposomes (100 L) were tangential flow filtered by passing them through two 2 ft² Microgon hollow fiber filters (in a parallel configuration) of 0.22 um pore size. An Alfa Laval rotary lobe pump was used to filter the product through the filters at an average flow rate through each filter of 15 gallons/minute. The filtration pressures were as follows: $P_{in}$=10 psig; $P_{out}$=2.5 psig. The pressure across the membrane was 5.5–6.0 psig. The filtration, which resulted in a final concentration of the original 100 L of sample to 20 L of product, proceeded at a flux rate of 0.6L/min. for 2.25 hours.

The product was then diafiltered to remove free (unentrapped) gentamicin by filtration through four Microgon filters in a parallel configuration. Physiological saline (20 L) was added to the holding tank containing the retentate from the 0.22 um tangential flow filtration step, and the retentate collected. This process was repeated 6 times, after which time the product contained 5.6 mg/ml of entrapped gentamicin in 20 L of product.

We claim:

1. A method of producing nonliposomal lipid particles of a homogeneous, defined size distribution from a mixture of lipid particles of heterogeneous size comprising the steps of:
    (a) subjecting the mixture to tangential flow filtration with a first filter of a first pore size;
    (b) subjecting the filtrate from step (a) to tangential flow filtration with a second filter of a second, smaller pore size; and
    (c) collecting the retentate from step (b),
        wherein the first pore size defines the upper limit of the size distribution of the liposomes or lipid particles, the first pore size is between about 10 and about 0.2 microns, the second pore size defines the lower limit of size distribution of the particles and the second pore size is between about 2000 molecular weight and about 2 microns.

2. The method of claim 1 wherein the lipid particles additionally comprise a bioactive agent.

3. The method of claim 2 wherein the bioactive agent comprises a polyene antifungal agent.

4. The method of claim 3 wherein the polyene antifungal agent comprises amphotericin B and wherein the lipid particles comprise a lipid which comprises dimyristoyl phosphatidylcholine and dimyristoyl phosphatidylglycerol.

5. The method of claim 1 wherein the first pore size is about 5 um.

6. The method of claim 1 wherein the second pore size is about 1.0 um.

7. The method of claim 1 further comprising the step of milling the lipid particles to reduce their size prior to their application to a tangential flow filter.

8. A population of lipid particles with a homogeneous defined size distribution prepared by tangential flow filtration in accordance with the method of claim 1.

9. The population of claim 8 wherein the lipid particles comprise a lipid and a bioactive agent.

10. A method of producing nonlipoosmal lipid particles of a size having sizes below a defined size cutoff comprising the steps of:
    (a) homogenizing the particles:
    (b) subjecting the particles to tangential flow filtration with a first filter of a pore size which excludes particles above the defined cutoff;
    (c) collecting the filtrate from step (b) and,
    (d) subjecting the collected filtrate from step (c) to tangential flow filtration with a second filter of smaller pore size.

11. A method for preparing a liposome or lipid particle comprising the step of contacting a solution containing lipid to a first side of a filter in tangential flow filtration apparatus while infusing or injecting an aqueous solution to a second side of the filter in the tangential flow filtration apparatus.

12. The method of claim 11 wherein the tangential flow filtration system employed is a dynamic rotary filtration or a hollow fiber filtration.

* * * * *